US007636718B1

(12) United States Patent
Steen et al.

(10) Patent No.: US 7,636,718 B1
(45) Date of Patent: Dec. 22, 2009

(54) PHARMACEUTICAL ADMINISTRATIVE SYSTEM FOR ORDERING AND RECEIVING PRESCRIBED MEDICATION

(75) Inventors: Eric K. Steen, South Pasadena, CA (US); William John Brandon, Hoover, AL (US); Thomas J. Wilverding, Davie, FL (US); Michael A. Koch, Foothill, CA (US); Jean Pfeiffer, Goleta, CA (US)

(73) Assignee: B. Braun Medical Inc., Bethlehem, PA (US)

( * ) Notice: Subject to any disclaimer, the term of this patent is extended or adjusted under 35 U.S.C. 154(b) by 335 days.

(21) Appl. No.: 09/650,482

(22) Filed: Aug. 29, 2000

Related U.S. Application Data

(60) Provisional application No. 60/158,261, filed on Oct. 7, 1999, provisional application No. 60/158,092, filed on Oct. 7, 1999, provisional application No. 60/158,214, filed on Oct. 7, 1999, provisional application No. 60/158,263, filed on Oct. 7, 1999.

(51) Int. Cl.
*G06F 17/30* (2006.01)
*G06F 7/00* (2006.01)
*G06F 17/00* (2006.01)
(52) U.S. Cl. .................... 707/100; 707/104.1; 700/235
(58) Field of Classification Search ................ 705/1–4, 705/9, 10, 26; 707/100, 104.1; 700/90, 231–236, 700/110, 239, 244; 709/213, 223, 224
See application file for complete search history.

(56) References Cited

U.S. PATENT DOCUMENTS

| 4,839,806 | A | * | 6/1989 | Goldfischer et al. ......... 700/231 |
| 4,847,764 | A | * | 7/1989 | Halvorson ................. 700/231 |
| 4,918,604 | A | * | 4/1990 | Baum ........................... 221/5 |
| 5,077,666 | A | * | 12/1991 | Brimm et al. .................. 705/2 |
| 5,208,762 | A | * | 5/1993 | Charhut et al. ............. 700/216 |
| 5,307,260 | A | * | 4/1994 | Watanabe et al. .............. 703/2 |
| 5,597,995 | A | * | 1/1997 | Williams et al. ............ 235/375 |
| 5,737,539 | A | * | 4/1998 | Edelson et al. ................. 705/3 |
| 5,748,907 | A | * | 5/1998 | Crane ............................. 705/2 |
| 5,758,095 | A | * | 5/1998 | Albaum et al. ................. 705/2 |
| 5,761,877 | A | * | 6/1998 | Quandt ........................ 53/155 |
| 5,832,488 | A | * | 11/1998 | Eberhardt .................... 707/10 |

(Continued)

OTHER PUBLICATIONS

On-line Medical Dictionary; http://cancerweb.ncl.ac.uk/cgi-bin/omd?query=electrolytes&action=Search+OMD; 1998; pp. 1-5.*

(Continued)

*Primary Examiner*—Ella Colbert
(74) *Attorney, Agent, or Firm*—Klein, O'Neill & Singh, LLP

(57) ABSTRACT

A pharmaceutical administrative system with a pharmacy and a service center network for preparing and dispensing medication. The pharmacy network prepares orders for medication from various customers for various patients. By retrieving information from a global database in the service center network, the pharmacy network conveys patient, customer and formulary information to users of the pharmacy network. Also, the pharmacy network prepares medication specific labels to identify and verify the contents of the medication. Furthermore, the pharmacy network provides additional safeguards and information, including balancing orders and displaying and/or generating hardcopies of solubility curves, to a health care provider using the pharmacy network with the additional ability to customize the medication.

25 Claims, 4 Drawing Sheets

U.S. PATENT DOCUMENTS

| | | | | |
|---|---|---|---|---|
| 5,845,255 A * | 12/1998 | Mayaud | ............................ | 705/3 |
| 5,899,998 A * | 5/1999 | McGauley et al. | ......... | 707/104.1 |
| 5,907,493 A * | 5/1999 | Boyer et al. | .................. | 700/231 |
| 5,924,074 A * | 7/1999 | Evans | ............................ | 705/3 |
| 5,950,630 A | 9/1999 | Portwood et al. | ............. | 128/897 |
| 5,970,462 A * | 10/1999 | Reichert | ......................... | 705/2 |
| 5,991,739 A * | 11/1999 | Cupps et al. | ................... | 705/26 |
| 6,014,631 A | 1/2000 | Teagarden et al. | .............. | 705/3 |
| 6,021,392 A | 2/2000 | Lester et al. | .................... | 705/2 |
| 6,070,761 A * | 6/2000 | Bloom et al. | .................. | 222/81 |
| 6,181,979 B1 * | 1/2001 | Murakami | ..................... | 700/216 |
| 6,317,719 B1 * | 11/2001 | Schrier et al. | .................... | 705/2 |
| 6,578,003 B1 * | 6/2003 | Camarda et al. | ................ | 705/3 |
| 2005/0107914 A1 * | 5/2005 | Engleson et al. | ............. | 700/237 |

OTHER PUBLICATIONS

Conlin, Robert; "CVS To Fill Online Orders For Merck-Medco"; E-Commerce Times; Oct. 6, 1999; pp. 1-3.*

Ghassemi, H. and Wunnava, S.; "Development of an operational medical network (MEDNET) model"; IEEE; Mar. 26-29, 1995; 162-164.*

Shane, R.; White, J.; and Saltiel, E.; "Maximizing The Use Of Pharmacists' Interventions"; ASHP Annual Meeting, V47; Jun. 1990; p. 1.*

* cited by examiner

PHARMACEUTICAL ADMINISTRATIVE SYSTEM FOR ORDERING AND RECEIVING PRESCRIBED MEDICATION

CROSS-REFERENCE TO RELATED APPLICATION(S)

This application claims the benefit of U.S. Provisional Application No. 60/158,261, filed Oct. 7, 1999, U.S. Provisional Application No. 60/158,092, filed Oct. 7, 1999, U.S. Provisional Application No. 60/158,214, filed Oct. 7, 1999, U.S. Provisional Application No. 60/158,263, filed Oct. 7, 1999, which are hereby incorporated by reference as if set forth in full herein.

BACKGROUND OF THE INVENTION

The present invention relates generally to pharmaceutical methods and systems for ordering and receiving prescribed medication, and in particular to methods and systems for providing information regarding prescribed medication and verifying that the prescribed medication is the medication shipped.

Generally, a pharmacy compounds and dispenses medication based on order of a physician. A health care pharmacy includes other features not generally found in most general pharmacies. Some features include, special administrative features, provision of drugs for nursing stations, manufacturing of pharmaceutical preparations, preparation and revision of a hospital formulary, and monitoring the drug regimen of the individual patient, i.e., clinical pharmacy. However, the additional features provided by the health care pharmacy come with an increased cost in the complexity of the pharmaceutical operations.

To assist in the reduction of the complexity of pharmaceutical operations, pharmaceutical administrative systems have been implemented. The conventional pharmaceutical administrative system allows a pharmacy to receive an order from a health care provider, such as a hospital, and assist the pharmacy in filling the order. Also, some pharmaceutical administrative systems provide information regarding potential side effects of a particular medication. However, the conventional pharmaceutical administrative system is often cumbersome to operate and not intuitive to a pharmacist or technician operating the computer system.

Also, generally, the conventional pharmaceutical administrative systems do not have "built-in checks" to assist the pharmacist or health care provider in dispensing or preparing prescribed medication. For instance, medications such as intravenous (IV) solutions require a specific mixture of ingredients. The incorrect amount of one ingredient, the wrong ingredient added to the IV solution or a combination of ordered ingredients that has unintended results may prove to be hazardous to the patient receiving the medication. Also, once an IV solution is prepared by the health care provider pharmacy, the health care provider upon receipt of the IV solution relies on the label on the IV solution to identify the medication. In other words, no safeguard to verify the contents of the IV solution is provided to ensure that the medication ordered by the health care provider is "actually" the medication shipped.

Furthermore, conventional pharmaceutical administrative systems are often limited in the information provided to the pharmacy and the health care provider regarding the potential risks and problems associated with a particular medication. For instance, an IV solution may contain high concentrations of an ingredient that if conveyed to the health care provider may cause the health care provider to order another medication. Alternatively, the health care provider may just want to customize the concentrations or ingredients of a medication based on the information about the particular medication.

Accordingly, there is a need for pharmaceutical administrative systems and methods in providing flexibility, without increased complexity, to the health care provider pharmacy in ordering and dispensing medication. Also, the pharmaceutical administrative systems and methods need to verify and provide safeguards to the health care provider to ensure that the medication is properly received and administered. Furthermore, the pharmaceutical administrative systems and methods should provide relevant information for a particular medication and the ability to customize the medication.

SUMMARY OF THE INVENTION

The present invention provides a pharmaceutical administrative system and method for performing a variety of pharmaceutical operations including preparing and dispensing medication. According to the present invention, the pharmaceutical administrative system is provided and comprises a pharmacy network and a service center network. The pharmacy network includes a pharmacy server and at least one pharmacy client system, the at least one pharmacy client system configured to accept and process orders for medications. The service center network includes a service center server and a service center client system, the service center network coupled to the pharmacy network and configured with a global database including a plurality of formulary records. In the embodiment described, the service center server supplies the pharmacy server at least one of the plurality of formulary records upon request by a pharmacy client system when an order is processed.

In another aspect, a pharmacy client system receiving and processing orders for medication is provided. The pharmacy client system comprises an order maintenance unit configured to create an order for medication for at least one customer and at least one patient and a formulary unit coupled to the order maintenance and presenting information about the medication to the order maintenance unit. The pharmacy client system also includes a customer unit coupled to the order maintenance unit and presenting information relating to contact and purchasing information for the at least one customer ordering the medication and a patient unit coupled to the order maintenance unit and the customer unit and presenting information relating to contact and medical information for the at least one patient. In the embodiment described, the order maintenance unit is configured to modify the ingredients of the medication and to validate the modifications to the ingredients of the medication.

In another embodiment, in a pharmaceutical administrative system, a method of dispensing medication comprises creating a record for an order for a medication, retrieving information regarding the medication, generating a medication specific label including information about the medication, and validating the order for the medication.

Many of the attendant features of this invention will be more readily appreciated as the same becomes better understood by reference to the following detailed description considered in connection with the accompanying drawings.

DETAILED DESCRIPTION OF THE INVENTION

Figure 1:
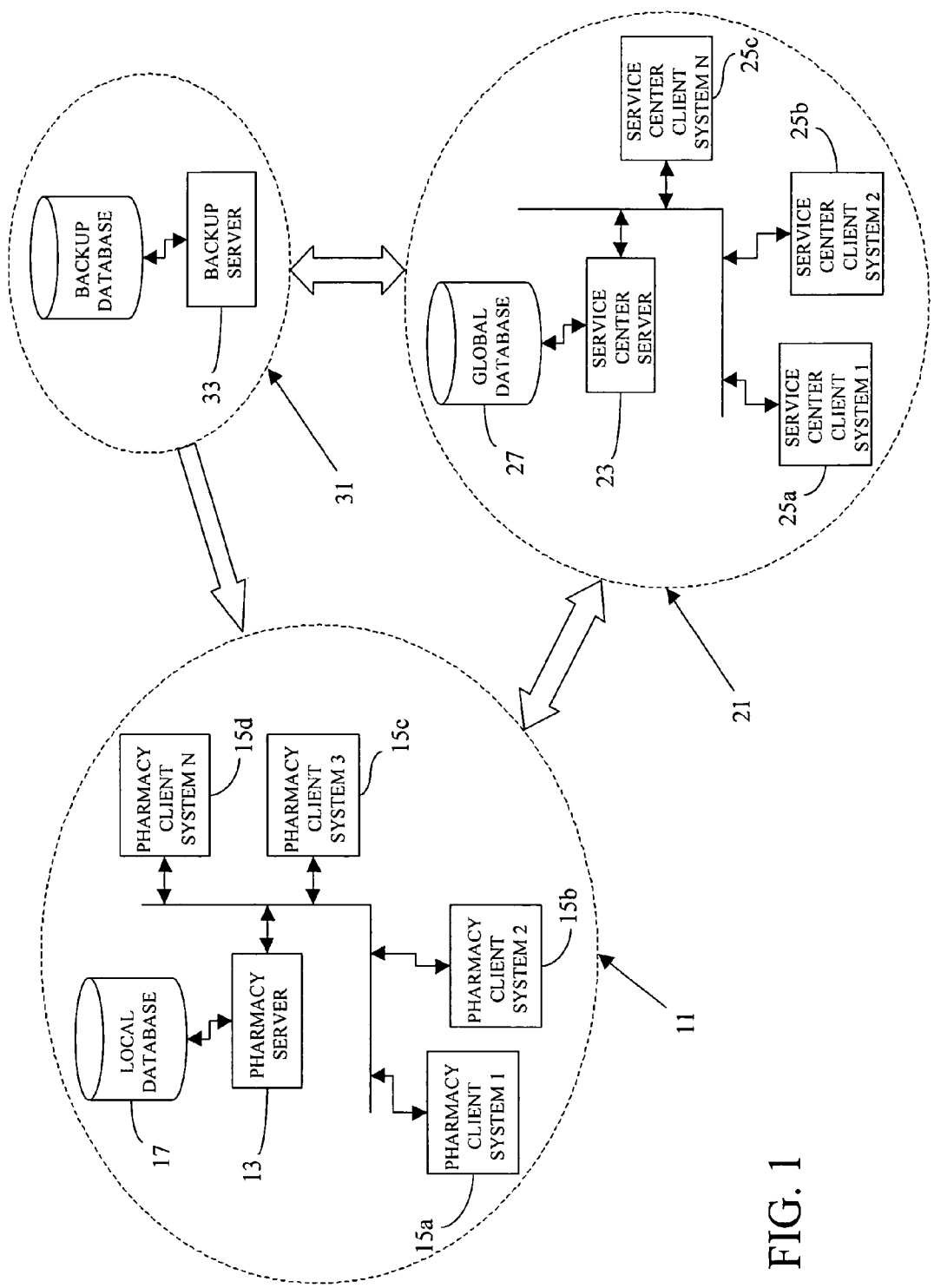
FIG. 1 illustrates a block diagram of one embodiment of a pharmaceutical administrative system of the present invention.

FIG. 1 illustrates a block diagram of one embodiment of the pharmacy administrative system of the present invention. The pharmacy administrative system includes a pharmacy network 11 and a service center network 21. In one embodiment, the pharmacy network 11 and service center network 21 are geographically located in different places and are coupled together via an Internet connection through network devices, such as routers or switches. The Internet connection might comprise telephone lines, ISDN lines, DSL lines, cable connections and the like. In one embodiment, the pharmacy network and the service center network are individual local area networks each having a router that is coupled to an Intranet through a leased line connection such as a T-1 type secure connection. In yet another embodiment, the connection is a modem connection between individual computers on the respective pharmacy and service center networks.

The pharmacy network 11 and the service center network 21 are each an interconnection of computing devices. The computing devices in the pharmacy network include a pharmacy server 13 and pharmacy client systems 15a-15d. The computing devices in the service center network 21 include a service center server 23 and service center client systems 25a-25c. For illustrative purposes, the number of pharmacy client systems and service client systems is limited, as it should be recognized that the number of computing devices may be exceedingly numerous. The pharmacy client systems 15a-15d and the service center client systems 25a-25c are computing devices such as personal computers, workstations, hand-held computers and the like.

The pharmacy server 13 is coupled and communicates with the pharmacy client systems 15a-15d over a local area network or a wide area network, using a wired communication media, such as coaxial cables or optical fibers or a wireless media, such as radio frequency (RF) communications. Similarly, the service center server 21 is coupled and communicates with the service center client systems 25a-25c over a local area network or a wide area network, using a wired communication media, such as coaxial cables or optical fibers or a wireless media, such as radio frequency (RF) communications.

In one embodiment, the pharmacy client systems 15a-15d are included or inside other networks mutually exclusive of the pharmacy network 11. Similarly, in one embodiment, the service center client systems 25a-25c are inside other networks mutually exclusive of the service center network 11. These other networks include other intranets or enterprise computing systems. Alternatively, these other networks include different network segments of the Internet. Furthermore, although the pharmacy administrative system in FIG. 1 illustrates one pharmacy network and one service center network, additional pharmacy and service center networks could be included. Moreover, the additional pharmacy networks could be grouped and coupled to one or more service center networks.

The pharmacy server 13 handles transactions between the pharmacy client systems 15a-15d and the pharmacy server 13. Specifically, the pharmacy server is configured to receive and process information from the pharmacy client systems. The information includes orders or requests for a specific type of medication or medications for a particular customer or patient. Also, the information includes details concerning the particular customer or patient. Medication orders that are placed by the pharmacy client system 15a-15d are transmitted to pharmacy server 13. The pharmacy server 13 then handles transactions between the pharmacy network 11 and one or more service center networks for processing of the medication orders.

Similar to the pharmacy server 13, the service center server 23 handles transactions between the service center network 21 and one or more pharmacy networks. The service center server receives the medication orders from the pharmacy server 13 and transmits information to the pharmacy server 13 to assist and permit the pharmacy server 13 to satisfy or dispense the medication orders. The information transmitted by the service center includes formulary, customer, patient and other various information pertaining to the order, such as shipping or handling instructions.

In one embodiment, the service center server 23 includes a service center network mass storage device for storing a global database 27. However, although described separately, the service center network mass storage device can be included in the service center server 23. The service center network mass storage device may take the form of a hard disk drive, a redundant array of independent disks (RAID), or a group of disk also known as "just a bunch of disks" (JBOD). The global database includes information pertaining to one or more pharmacy networks, such as records of the transactions between the service center network 21 and the pharmacy network 11. The global database further includes specific information concerning a particular request or order from a particular pharmacy for a particular patient and/or customer as well as formulary information for a customer of a specific pharmacy. Hence, the service center network 21 acts as a central repository of information for one or more pharmacy networks.

Similar to the service center server 23, the pharmacy server 13 also includes a pharmacy network mass storage device that may take the form of a hard disk drive, a RAID, or JBOD. However, although described separately, the pharmacy network mass storage device can be included in the pharmacy server 13. The pharmacy network mass storage device stores a local database 17 that contains information, specifically replicated information for a given pharmacy from the service center server. The local database 17 also includes information on the availability and identity of the service center network 21 and other service center networks. Therefore, the local database 17 acts as a "fail-safe" database to handle transactions from the pharmacy clients 15a-15d, if the service center network 21 becomes unavailable.

In one embodiment, the pharmacy administrative system also includes a backup network 31. The backup network 31 includes a backup server 33. In one embodiment, the backup network also includes a network device, such as a router or switch, coupling the backup network to the pharmacy network 11 and the service center network 21. The backup network 31 ensures that the pharmacy network is able to operate if the service center network is unavailable for a predetermined time period. The backup server receives data from the service center network. The data is replicated data of information pertaining to one or more pharmacy networks. The backup server is configured to identify and categorize the data from the service center network for a specific pharmacy network. The backup server is further configured to transmit copies of the data subset to that specific pharmacy network.

The backup server repeatedly updates the pharmacy networks as often as updates of data from the service center is provided to the backup network. In the event that a connection is lost between the service center and the pharmacy network, the pharmacy network is capable of operating autonomously and with a minimal loss of data. The loss of data is limited to the last update of data provided by the backup network. Also, the backup network is capable of acting as a replacement for the service center until connection between the pharmacy network and the service center network is once again re-established.

Figure 2:
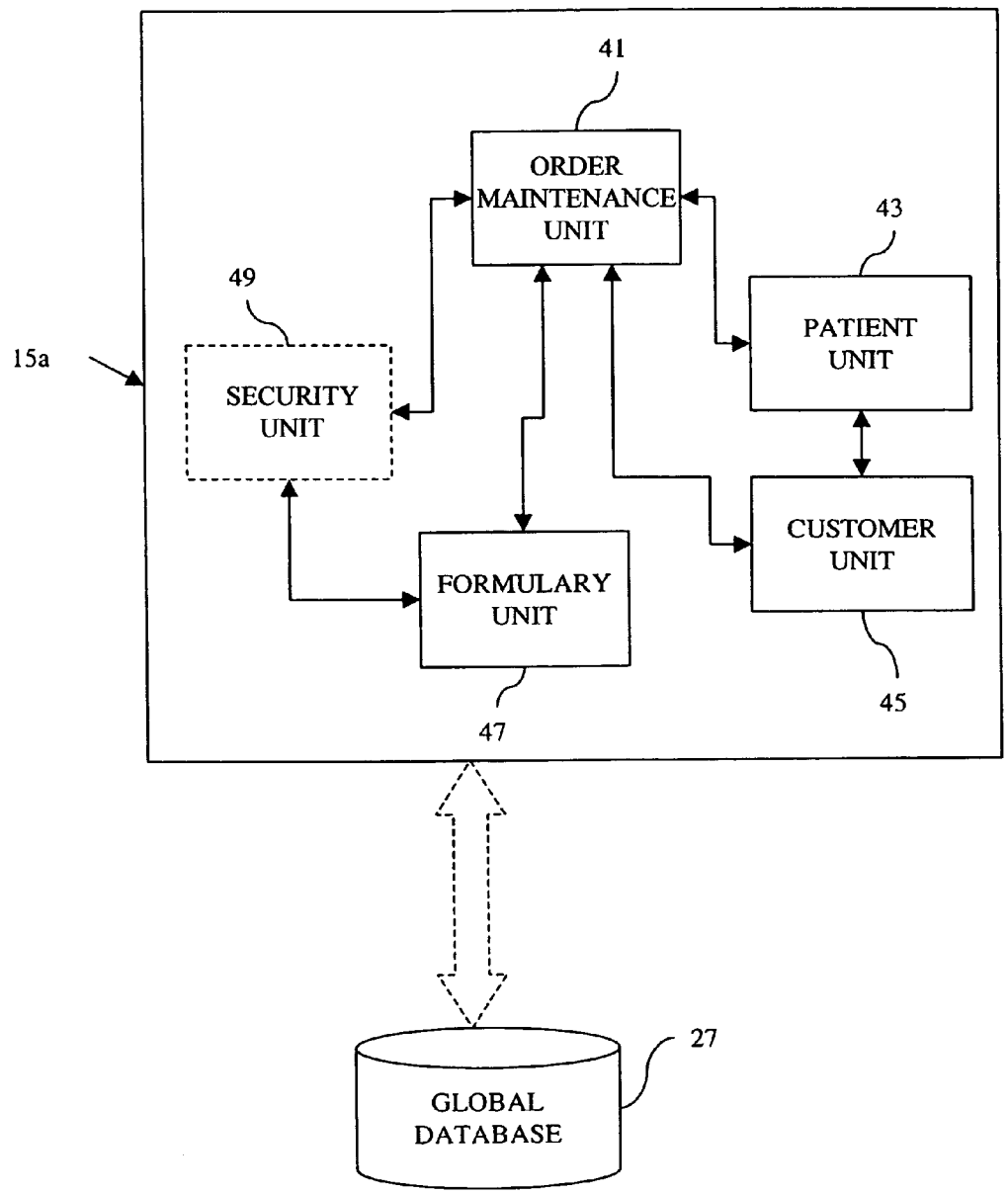
FIG. 2 illustrates a block diagram of one embodiment of a pharmacy client system of the present invention.

Turning now to FIG. 2, a block diagram of one embodiment of a pharmacy client system of the present invention is shown. The pharmacy client system 15a of the present invention is configured to place a medication order. In the process of placing the medication order, which is transmitted to the pharmacy server 13, the pharmacy client system requires specific information relating to the customer, patient or formulary. The pharmacy client system is capable of obtaining the required specific information through manual input. Likewise, the pharmacy server 13 is also capable of obtaining the required specific information by retrieving the information from the local database 17. However, preferably, the required information is provided by the pharmacy server 13 in which the pharmacy server retrieves the information from the global database 27 in the service center network 21.

The global database contains information that assist a health care provider pharmacy with transactions necessary for performing pharmaceutical operations. The information in the global database is in the form of a series of records. The pharmacy client system 15a includes five operational units to manage the information or records from the global database and to handle transactions between pharmacy client systems and the pharmacy server 13. The four operational units are order maintenance unit 41, patient unit 43, customer unit 45 and formulary unit 47.

Instructions and data, i.e., input, are provided to the four operational units by the pharmacy client systems through various interfaces. In one instance, input is entered through one or more user-interface windows or screens on a pharmacy client system responding to events or actions performed by a keyboard or touch-screen and a mouse. Input can also be entered through remote devices by wired or wireless modems and remote sites through network connections, such as through the Internet.

The order maintenance unit 41 is configured to receive input and provide information for an order of a specific medication or a group of medications. Specifically, the order maintenance unit 41 is configured to define and provide specific information for a specific order. For instance, the order maintenance unit 41 is configured, in one embodiment, to define electrolyte information for an order, such as setting acetate and chloride percentages, defining whether the cation is sodium or potassium, defining whether the calcium used is CaCl or CaGlu and defining base elements to be added to the order. Each order creates a record that is stored in the global database.

The order maintenance unit 41 is also configured to assign miscellaneous information, such as handling, shipping, and administrative instructions for a specific order. The order maintenance unit 41 is further configured to provide a list of ingredients that make up a particular order. The order maintenance unit is also able to request for an order, carbohydrates and lipids, protein and ingredients by calories. In one embodiment, proprietary or pre-existing interfaces, such as a flat or otherwise pre-formatted file uploaded to the pharmacy client systems, are also capable of providing entries to place an order for a medication.

The order maintenance unit 41 is also configured with a search engine to retrieve information about a particular order or orders. The search engine by using a search term or parameter such as a patient's name, identification number or customer is configured to retrieve the associated record for the particular order or orders.

As shown in FIG. 2, the order maintenance unit 41 is coupled to the patient unit 43 and the customer unit 45. The patient unit 43 manages information about individual patients. For instance, patient information includes physical and medical information of a patient such as current medications, allergies, personal contact and admission information and physician contact information. The patient information further includes demographic information relating to the patient's date-of-birth, family status, age, gender and the like. The patient unit 43 is also configured with a search engine to retrieve information about a particular patient, i.e., a patient profile. The search engine by using a parameter such as a patient's name, identification number or customer is configured to retrieve the associated record. Patient information is stored as records in the global database. When a new patient, i.e., a patient previously unknown to the pharmacy administrative system, requires a medication, a new record is created and stored in the global database by the patient unit.

The customer unit 45 manages information about specific health care provider using the services of a specific pharmacy and thereby conducting transactions with a specific pharmacy network. The customer unit maintains and manages records of contact, billing, shipping and IV solution vendor information for a particular customer, such as a clinic or hospital. Also, the customer unit is configured to create, modify and remove formulary items and ingredients related to the formulary items that a customer can order. Information concerning shelf lives and dose range limits for each formulary item is also provided by the customer unit. The customer unit 45 is further configured to create, modify and remove administration and handling instructions for a particular customer. Any cross reference list defining names for formulary items which a customer uses and frequency of administration of a medication to a patient can be accomplished by the customer unit.

Similar to the patient unit 43, the customer unit 45 is also configured with a search engine to retrieve a customer profile, i.e., information about a particular customer. The search engine by using a parameter such as a customer's name, identification number is configured to retrieve the associated record. Also, similar to the patient unit, customer information is stored as records in the global database. Likewise, when a new customer, i.e., a customer previously unknown to the pharmacy administrative system, requires a medication, a new record is created and stored in the global database by the patient unit.

The formulary unit 47 manages information and calculations concerning medication ordered by a specific pharmacy. Additionally, the formulary unit is configured to perform therapeutic checks. The formulary unit is further configured to create, modify and remove records regarding specific drug information (drug category, dosage form, route of administration, and specific gravity), limits (shelf life and minimum and maximum dose levels), electrolyte and salt content information, dilution levels of a specific medication and national drug code (NDC) information. In one embodiment, the formulary unit provides conversion algorithms for converting one unit to another unit, i.e., milliliter to kilocarlorie. Similar to the patient unit, the formulary unit also includes a search engine to retrieve information about a particular medication for a particular order. The search engine by using parameters such as formulary names, categories, or drug codes is configured to retrieve the associated record.

In one embodiment, the pharmacy client system also includes a security unit 49. The security unit validates or confirms access to one of the other four operational units of the pharmacy client system. The security unit 49 is configured to assign unique numeric identification to users of the pharmacy client systems. Through authentication schemes, such as login or password procedures, the security unit 49 maintains the integrity of the pharmacy client systems and the information maintained therein. The operational units, although described separately, can be configured as a single unit or as a single computing device with a software program incorporating the before mentioned units.

Figure 3:
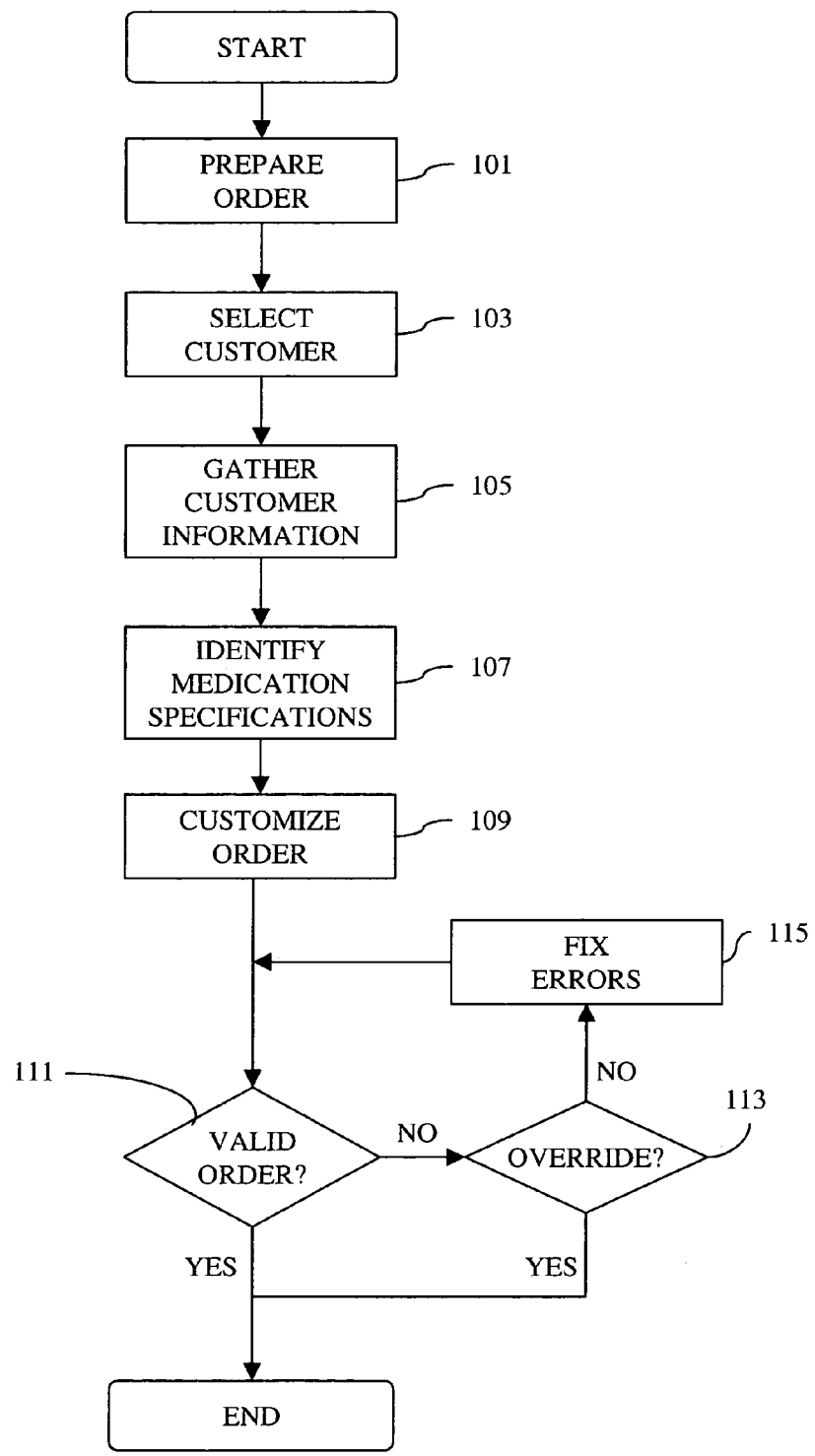
FIG. 3 illustrates a flow diagram of one embodiment of an overview process of dispensing medication by a pharmaceutical administrative system of the present invention.
Figure 4:
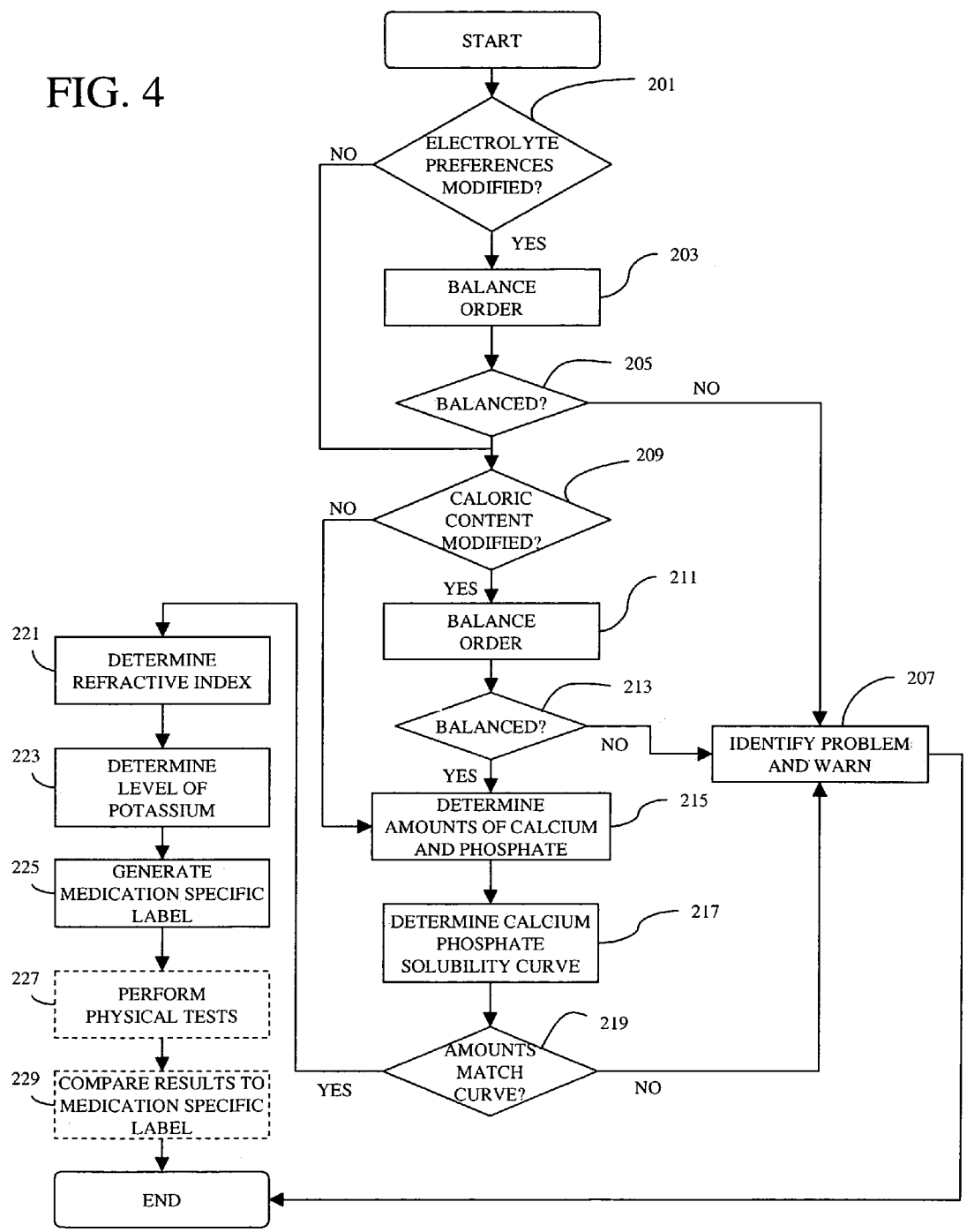
FIG. 4 illustrates a flow diagram of one embodiment of detailed process of verifying medication ordered by the pharmaceutical administrative system of the present invention.

FIG. 3 illustrates a flow diagram of one embodiment of operating the pharmacy administrative system of the present invention. In step 101, an order is prepared through the pharmacy network. In step 103, a customer is selected. In one embodiment, a patient is selected and an associated customer is automatically determined and selected. In step 105, customer information is gathered from the customer unit. In step 107, based on the order, specifically the drug being ordered, the formulary unit identifies ingredients within the specific drug. In step 109, the option is provided to customize the order and any information related to the order such as the ingredients of the drug or customer contact information. Based on the order and any customization of the order, the order maintenance unit validates the order using a subroutine or sub-process as shown in FIG. 4. In step 111, the order maintenance unit determines if the order is valid or invalid. If the order is validated, then the order proceeds along in which a medication specific label can be generated or a solubility curve can be viewed and then the process ends once the order is placed.

However, if, in step 111, the order maintenance unit does not validate the order, then in step 113, the order maintenance unit can be commanded by the user, e.g., the pharmacist, to override the invalidation. As a result, a medication specific label can be generated or a solubility curve can be viewed and then the process ends once the order is placed. However, if in step 113, the invalidation is not overridden, then the order maintenance unit notes the improper entries and provides re-entry of the information, in step 115. Once the re-entry of information is complete, the process repeats by once again validating the order in step 111.

Turning back again to the order maintenance unit 41 of FIG. 2, the order maintenance unit is further configured to provide additional safety and convenience features for the pharmacy administrative system. These features include generating medication specific labels, especially for intravenous (IV) solutions, for customers or patients and notifying and warning a user, such as a pharmacist, at a pharmacy client system concerning potential problems or issues with a medication ordered.

In one embodiment, the order maintenance unit is further configured to permit customization of ingredients to a medication based on their caloric content. The order maintenance unit allows for the selection of the amount of carbohydrates, lipids, proteins, types of proteins and formulary items. Once selections have been made for a particular medication for an order, the order maintenance unit is capable of balancing the order. Balancing the order ensures that no errors have been made in the customization of the medication. If the medication does not balance, the order maintenance unit notifies and warns the user, e.g., the pharmacists, that an error in the customized medication has occurred.

In one embodiment, the validation of the medication includes balancing electrolytes in a medication. An electrolyte is a material that conducts an electric current when it is fused or dissolved in a solvent, usually water. Electrolytes are composed of positively charged species, called cations, and negatively charged species, called anions. For example, sodium chloride (NaCl) is an electrolyte composed of sodium cations (Na+) and chlorine anions (Cl−).

As such, the order maintenance unit is configured to allow for the selection of the amount of acetate to chloride ratio, cation preference and calcium preference. Once selections have been made for a particular medication for an order, the order maintenance unit validates, i.e., balances the order. Balancing the order ensures that no errors have been made in the selection of the electrolytes in the medication. If the medication does not balance, the order maintenance unit notifies and warns the user, e.g., the pharmacists, that an error in the selection of the electrolytes has occurred. In one embodiment, the global database contains default values for the electrolytes for a specific medication that are initially used by the order maintenance unit.

For an order, the order maintenance unit 41 generates a medication specific label based on the information stored in the global database. The medication specific label is outputted or printed through a conventional printer. The medication specific label is then affixed to the medication ordered. The medication specific label identifies particular information about the medication, such as ingredients, and other information such as customer and patient names. For IV solutions, in particular, information is provided on the medication specific label concerning mixture of ingredients, compatibility of ingredients, temperature and precipitation warnings, drug interactions and pH requirements.

Also, for an intravenous solution, additional validation operations can be performed to ensure the integrity and accuracy of the medication based on the medication specific labels. In one embodiment, a refractive index of an IV solution is calculated and the calculated refractive index is stored in the global database. The order maintenance unit then retrieves the calculated refractive index from the global database for the specific medication and order. Furthermore, the order maintenance unit generates a medication specific label containing the refractive index for the IV solution thereon.

Hence, once the medication specific label is affixed to the IV solution, a pharmacy or any customer, such as a hospital, can verify the integrity of the IV solution. For instance, the pharmacy or hospital can measure the refractive index of the IV solution and compare the measured refractive index to the printed refractive index on the medication specific label. If the indexes match, then the pharmacy or hospital can be assured that the IV solution is as labeled. However, if the indexes do not match then the pharmacy or hospital is alerted to the fact that the IV solution is wrongly labeled and thus should not be used.

In one embodiment, flame photometry is used for intravenous solution to establish the presence or absence of an element, potassium. Flame photometry is used to calculate the level of potassium in an IV solution and the calculated level of potassium is recorded in the global database for the IV solution. The order maintenance unit retrieves the calculated flame photometry from the global database for the specific medication, i.e., the IV solution, and for a specific order.

Furthermore, the order maintenance unit generates a medication specific label containing the calculated level of potassium for the IV solution thereon.

Hence, the pharmacy can verify the level of potassium in the IV solution. In one embodiment, when the medication reaches its destination, i.e., a hospital, the hospital can verify the level of potassium in the IV solution. For instance, the hospital or pharmacy can measure the level of potassium using a standard test station and compare the measured level of potassium to the printed level of potassium on the medication specific label. Therefore, if the levels match, then the hospital or pharmacy can be assured that the IV solution is as labeled. If the levels do not match, the hospital or pharmacy can make an informed determination if the level of potassium in the IV solution is acceptable.

The extent to which a component can be separated from solution can be determined from the solubility product constant obtained by determining the quantity of dissolved substance present in a known amount of saturated solution. This value is known as the solubility. The solubility can be drastically altered merely by adding to the solution any of the ions that make up the precipitate. Although solubility can be altered over a wide range, the solubility product itself remains practically constant over this same range. The solubility is critical because an IV solution that precipitates can extremely harmful to a patient.

Where a medication being ordered contains phosphate and/or calcium, in one embodiment, the order maintenance unit is configured to create and view solubility curves for a selected brand of amino acid, dextrose, and drug additive. The order maintenance unit receives data set entries to identify the amino acid, dextrose and drug additive and to define the amount or percentages of each item. Once the data set entries have been assigned for a particular medication for an order and during a validation of the order, the order maintenance unit is capable of generating a calcium phosphate solubility curve based on the data set entries.

In one embodiment, a graphical representation of the calculated calcium phosphate solubility curve is displayed or plotted and presented to the pharmacy client system via a user interface screen or window. In a further embodiment, a printout of the calculated calcium phosphate solubility curve is provided to a user of the pharmacy client system. As such, a printout of the calculated calcium phosphate solubility curve can be included in a patient's chart or file. In another embodiment, a calcium phosphate solubility curve is determined by examining the global database for curve data that matches or closely matches the percentages of the selected amino acid, dextrose, and drug additive. In one embodiment, other calcium phosphate solubility curves within the range of the calculated calcium phosphate solubility curve that are stored in the global database are identified and are available to the order maintenance unit to be selectively viewed.

The amount of calcium phosphate in the medication for the order is then determined by the order maintenance unit. If the amount of calcium phosphate is above the calcium phosphate solubility curve, then the calcium phosphate will cause precipitation, i.e., the process of producing a separable solid phase within a liquid medium. Therefore, the order maintenance unit notifies and warns the user, e.g., the pharmacists, that an error in the amount of calcium phosphate in the medication has occurred.

In one embodiment, in the event a calcium phosphate solubility curve cannot be identified, the ratio of calcium to phosphate is determined. The ratio of calcium to phosphate is then compared to a predetermined acceptable amount of calcium and phosphate for the medication from the global database. As such, if the ratio of calcium to phosphate exceeds the acceptable amount of calcium and phosphate, the order maintenance unit notifies and warns the user that an error has occurred. The error being that the amount of calcium phosphate in the medication is too high. Although the order maintenance unit will notify and warn a user regarding an error in the validation of the order, the order maintenance provides the user the ability to override, i.e., disregard, the error.

Referring now to FIG. 4, a flow diagram of one embodiment of a sub-process for validating an order for a medication or medications is shown. In step 201, the sub-process determines if the electrolyte preferences of the medication have been modified. If, in step 201, the sub-process determines that the electrolyte preferences of the medication have been modified, then the order is balanced in step 203 and, in step 205, the sub-process determines if the order balances. For instance, the amount of acetate to chloride ratio is evaluated and compared to a predetermined acceptable value for the amount. If the ratio exceeds the acceptable value, the sub-process notes the problem and issues a warning, in step 207, and then the sub-process ends. If, in step 201, the sub-process determines that the electrolyte preferences of the medication have not been modified, then the process continues to step 209. Likewise if, in step 205, the sub-process determines that the order balances, then the process continues to step 209.

In step 209, the sub-process determines if the caloric content of the medication has been modified, then the order is balanced in step 211 and, in step 213, the sub-process determines if the order balances. For instance, the amount of lipids is evaluated and compared to a predetermined acceptable value for the amount for the prescribed medication. If the amount of lipids exceeds the acceptable value, the sub-process notes the problem and issues a warning, in step 207, and then the sub-process ends. If, in step 209, the sub-process determines that the caloric content of the medication has not been modified, then the process continues to step 215. Likewise if, in step 213, the sub-process determines that the order balances, then the process continues to step 215.

In step 215, the amount of calcium and phosphate in the medication is determined. If no calcium or phosphate are in the medication, then the process continues to step 221. In step 215, based on the amount of calcium and phosphate determined, the calcium phosphate solubility curve is calculated in step 217. In step 219, calcium phosphate solubility of the medication is identified and compared to the calculated calcium phosphate solubility curve. If the amount of calcium phosphate exceeds or above the calculated phosphate solubility curve, the sub-process notes the problem and issues a warning, in step 207, and then the sub-process ends. If, in step 219, the sub-process determines that the amount of calcium phosphate is below or on the calculated phosphate solubility curve, then the process continues to step 221.

In step 221, the process determines the refractive index for the IV solution by calculation as described above. The process then, in step 223, determines the level of potassium in the IV solution by calculation as described above. In step 225, the process, generates a medication specific label including the calculated refractive index and the calculated level of potassium of the IV solution. In step 227, physical tests are performed. In one embodiment, as described above, a physical test is performed by a pharmacy or a customer, such as a hospital, to determine the refractive index of the IV solution. In one embodiment, also described above, a physical test is, also or alternatively, performed by the pharmacy or hospital to determine the potassium level of the IV solution. In one embodiment, the pharmacy or hospital uses flame photometry to determine the potassium level of the IV solution. Once the physical tests are completed, the pharmacy or hospital compares the results of the physical tests to the information on the medication labels, e.g., the potassium level and/or the refractive index, in step 229 and then the sub-process ends. Subsequently, if the results of the physical tests do not match the information on the medication labels, then the pharmacy or hospital is able to take the appropriate action, such as not using and re-ordering or re-make the IV solution.

Accordingly, the present invention provides a pharmaceutical administrative system and methods that provide increased flexibility in features with greater safeguards. Although this invention has been described in certain specific embodiments, many additional modifications and variations would be apparent to those skilled in the art. It is therefore to be understood that this invention may be practiced otherwise than as specifically described. Thus, the present embodiments of the invention should be considered in all respects as illustrative and not restrictive, the scope of the invention to be determined by the appended claims and their equivalents rather than the foregoing description.

The invention claimed is:

1. A pharmaceutical administrative system comprising: a pharmacy network including a pharmacy server and at least one pharmacy client system, the at least one pharmacy client system configured to accept and process orders for medications; and
   a service center network including a service center server the service center network coupled to the pharmacy network and configured with a global database including a plurality of formulary records: wherein the service center server is configured to supply the pharmacy server at least one of the plurality of formulary records for at least one of the orders for medication upon request by the at least one pharmacy client system when the at least one of the orders for medication is processed, and wherein the pharmacy client system is further configured to generate a medication specific label containing medication composition information.

2. The pharmaceutical administrative system of claim 1 wherein the global database further includes a plurality of order records, each order record including order information for an order accepted and processed by the at least one pharmacy client system.

3. The pharmaceutical administrative system of claim 1 wherein the global database further includes a plurality of customer records, each customer record including contact and formulary information for at least one customer.

4. The pharmaceutical administrative system of claim 2 wherein the global database further includes a plurality of patient records, each patient record including contact information and medication history for at least one patient.

5. Tile pharmaceutical administrative system of claim 3 wherein the pharmacy client system is configured to provide updates to the patient, customer, and formulary records in the global database.

6. The pharmaceutical administrative system of claim 5 wherein updates to the formulary records include modification to the ingredients of the medication.

7. The pharmaceutical administrative system of claim 6 wherein updates to the modification to the ingredients of the medication include changes to amounts of caloric content in the medication.

8. The pharmaceutical administrative system of claim 6 wherein updates to the modification to the ingredients of the medication include changes to amounts and preferences of electrolytes in the medication.

9. The pharmaceutical administrative system of claim 6 wherein the pharmacy client system is configured to verify the updates to the formulary records in the global database.

10. The pharmaceutical administrative system of claim 6 wherein the medication specific label is for an intravenous solution and the medication identification information includes a refractive index associated with the intravenous solution.

11. The pharmaceutical administrative system of claim 6 wherein the medication specific label is for an intravenous solution and the medication identification information includes a level of potassium associated with the intravenous solution.

12. The pharmaceutical administrative system of claim 6 wherein the pharmacy client system is configured to generate a calcium phosphate solubility curve for an order accepted and processed by the at least one pharmacy client.

13. The pharmaceutical administrative system of claim 5 further comprising:
   a backup network configured to provide access to a backup database by the pharmacy network when the service center network is not available for a predetermined amount of time, the backup network comprising:
   a backup server configured to:
   receive replicated records of orders for medications, the replicated records of orders for medications being replicated by the service center server: and
   store in the backup database the replicated records of orders for medications.

14. The pharmaceutical administrative system of claim 5 wherein the pharmacy server is configured with a local database containing a subset of formulary records of the plurality of formulary records in the global database that specifically pertains to the pharmacy network.

15. The pharmaceutical administrative system of claim 1 wherein the medication is an intravenous solution.

16. The pharmaceutical administrative system of claim 15 wherein the pharmacy client system is configured to validate the modifications to the ingredients by generating a calcium phosphate solubility curve for the medication.

17. The pharmaceutical administrative system of claim 16 wherein the pharmacy client system is further configured to determine calcium and phosphate content in the medication and to compare the calcium and phosphate
   content to the calcium phosphate solubility curve for the medication.

18. The pharmaceutical administrative system of claim 17 wherein the pharmacy client system is further configured to provide a warning when the calcium and phosphate content does not match the calcium phosphate solubility curve for the medication.

19. The pharmaceutical administrative system of claim 18 wherein the pharmacy client system is configured to generate medication specific labels for the medication.

20. The pharmaceutical administrative system of claim 19 wherein the medication specific labels for the medication includes information about a refractive index of the intravenous solution.

21. The pharmaceutical administrative system of claim 20 wherein the medication specific labels for the medication includes information about a level of potassium in the intravenous solution calculated using flame photometry.

22. The pharmaceutical administrative system of claim 21 wherein the modifications to the ingredients of the medication includes modifications to caloric content of the medication.

23. The pharmaceutical administrative system of claim 22 wherein the pharmacy client system is configured to validate the modifications to the caloric content in the medication by comparing the modifications to predetermined amounts of caloric content in predefined medications.

24. The pharmaceutical administrative system of claim 21 wherein the modifications to the ingredients of the medication includes modifications to electrolytes in the medication.

25. The pharmaceutical administrative system of claim 24 wherein the pharmacy client system is configured to validate the modifications to the electrolytes in the medication by comparing the modifications to predetermined amounts of electrolytes in predefined medications.

* * * * *